United States Patent [19]
Madec et al.

[11] Patent Number: 5,573,947
[45] Date of Patent: Nov. 12, 1996

[54] SELECTIVE MEDIUM CONTAINING LITHIUM AND A POLYOL OR ANTIBIOTIC FOR COUNTING PROPIONIC BACTERIA

[75] Inventors: Marie-Noëlle Madec; Annette Rouault, both of Rennes; Jean-Louis Maubois, Pace; Anne Thierry, Romille, all of France

[73] Assignee: Institut National de la Recherche Agronomique, Paris, France

[21] Appl. No.: 302,930

[22] PCT Filed: Jan. 24, 1994

[86] PCT No.: PCT/FR94/00082

§ 371 Date: Sep. 22, 1994

§ 102(e) Date: Sep. 22, 1994

[87] PCT Pub. No.: WO94/17201

PCT Pub. Date: Aug. 4, 1994

[30] Foreign Application Priority Data

Jan. 27, 1993 [FR] France ................... 93 00823

[51] Int. Cl.⁶ ................ C12N 1/00; C12N 1/20
[52] U.S. Cl. .................. 435/253.6; 435/253.6; 435/243; 435/244; 435/252.4
[58] Field of Search ................ 435/243, 253.6, 435/244, 252.4

[56] References Cited

U.S. PATENT DOCUMENTS

| | | | |
|---|---|---|---|
| 4,278,663 | 7/1981 | Liu et al. | 424/119 |
| 4,368,265 | 1/1983 | Liu et al. | 435/75 |
| 4,798,726 | 1/1989 | Lagarde | 426/40 |
| 4,978,656 | 12/1990 | Blizzard et al. | 514/63 |
| 5,026,647 | 6/1991 | Tomes et al. | 435/244 |
| 5,232,838 | 8/1993 | Nelson et al. | 435/30 |

OTHER PUBLICATIONS

"Manual of Industrial Microbiology and Biotechnology", Chapter 9, pp. 97 and 109, 1986 technical notice (two pages) API System, 1989.
Microbiology, 1986 pp. 161–166.

*Primary Examiner*—David M. Naff
*Assistant Examiner*—Deborah K. Ware
*Attorney, Agent, or Firm*—Jacobson, Price, Holman & Stern, PLLC

[57] ABSTRACT

A medium is prepared for counting propionic bacteria under anaerobic conditions. The medium contains a complex culture medium composed in particular of a casein hydrolysate and a yeast extract, supplemented with at least one lithium compound, such as lithium lactate, and at least one polyol and/or one or more antibiotics. The counting of the bacteria in a biological sample is carried out by incubation of a sample or decimal dilutions of it in a counting medium.

18 Claims, No Drawings

SELECTIVE MEDIUM CONTAINING LITHIUM AND A POLYOL OR ANTIBIOTIC FOR COUNTING PROPIONIC BACTERIA

The object of the present invention is a selective medium for counting or enumerating propionic bacteria.

It also relates to a method for counting these microorganisms.

The propionic bacteria have an essential role in producing the organoleptic characteristics specific to cooked pressed crust cheeses (Emmental-Gruyère-Comté). They are involved in the production of $CO_2$ causing the formation of the "holes", in the production of acetic and, in particular, propionic acids, and in the peptic degradation of milk protein derivatives, both of which contribute to the characteristic flavor.

This bacterial genus has also been used recently for the industrial production of vitamin $B_{12}$. Other uses have also been suggested: production of propionates in a bioreactor (French patent n° 90 04 985 publication 2.660.932), said propionates being used for their antifungal properties in bread and cheese making, and production of biomass for probiotic use (feed for milk cows; preservation of silage).

Whether for these uses or for the determination of the role played in the maturing of pressed-crust cheeses, the progress of knowledge on propionic bacteria requires a specific means of counting, that is to say a selective culture medium.

To the knowledge of the applicant, no such selective medium exists.

The reference medium, currently used in the cheese industry, is the YELA (Yeast Extract Lactate Agar) medium described by Hettinga et al., 1968 (J. Dairy Science, 51 1707–1709). This medium enables propionic flora to be counted when they are predominant. However, it does not inhibit the mesophilic and thermophilic lactic bacteria which constitute the dominant flora in cooked pressed crust cheeses.

Two other media, based on the limitation of nitrogenous nutrients (replacement of the yeast extract by ammonium sulfate or a tryptic hydrolysate of casein, trypticase) and the corresponding provision of significant quantities of vitamins (biotin, calcium pantothenate, para-aminobenzoic acid and thiamine) and salts of essential minerals (in particular $Mg^{++}$; $Mn^{++}$ and $Fe^{++}$) have been described by Peberdy and Fryer (NZ J. Dairy Science and Techn., 11, 10–15, 1976). These media, named A.S.L.A. (Ammonium Sulfate Lactate Agar) and T.L.A. (Trypticase Lactate Agar), although showing relative selectivity, require at least 10 days anaerobic incubation and in addition must be used in parallel to count the propionic bacteria present in the cheeses. These practical limitations have been considered unacceptable by potential users and the use of the ASLA and TLA media has not developed further.

The addition of cadmium or a mixture of arsenic salts and an antibiotic, netilmicin, to a lactate agar medium (U.S. Pat. 5,026,647) has also been proposed.

However, these media only allow the growth of a limited number of strains belonging to the species P. jensenii and seem to inhibit the other propionic bacteria species.

In addition, the generalized use of these media would obviously create serious toxicity risks both for the operators and for the environment resulting from the discharge of arsenic and cadmium.

The milk propionic bacteria are known to be resistant to the majority of the sulfamides, to some penicillins of the penicillin-M group, such as oxacillin or cloxacillin, as well as to nalidixic acid (Reddy et al; 1972, J. Dairy Sci 55, 665; 1973, J. Milk Food Technol. 30, 564–569; 1973, Antimicrob. Ag. Chemother. 4, 254–258). The same authors have shown that the strains of Propionibacterium tested also showed moderate resistance to polypeptides (colistin and polymyxin B) and to antibiotics of the aminoside group (neomycin and kanamycin). The propionic bacteria are, on the other hand, sensitive to the majority of the β-lactamines (penicillin G and A, cephalosporins) as well as to the cyclines (tetracycline), and to the macrolides, such as erythromycin and to chloramphenicol (Reddy et al., J. Milk Food Technol. 30,564–569; Nord and Olsson-Liljequist, 1985, J. Antimicrob. Chemother., 15, suppl. C, 183–188). As far as the cutaneous strains of Propionibacterium are concerned, the use of antibiotics from the macrolide (erythromycin), lincosamide (lincomycin) and cycline groups (tetracycline) in acne treatment has led to the emergence of resistant strains, which has necessitated the use of other antibiotics (Eady et al., 1989. J. Antimicrob. Chemother., 23, 493–502; Eady et al., 1993, Br. J. Dermatol. 128, 556–560; Kurasawa et al., 1988, J. Dermatol. 15, 149–154). A selective medium has been proposed for the isolation of the wild and antibiotic-resistant strains of Propionibacterium acnes (Marino and Stoughton, 1982, J. American Acad. Dermatol., 6, 902–908).

The work of Reddy et al. (1972 and 1973, referred to above) has been subsequently used in the U.S. Pat. 5,026,647 and in the work of Drinan and Cogan-(1992, J. Dairy Research, 59, 65–9) aimed at developing selective media for counting milk propionic bacteria.

Thus, Cogan and Drinan (1992) have proposed adding an antibiotic, cloxacillin, to the SLA (Sodium Lactate Agar) medium. This antibiotic inhibits the growth of the lactic ferments present in the cheese, but, according to the authors, does not inhibit the growth of mesophilic lactobacilli, enterococci and Clostridium, microorganisms frequently found in cheeses.

The addition of nalidixic acid (0.02% w/v) to a medium containing yeast extract, sodium lactate and agar has recently been used to detect propionic bacteria in Leerdammer cheese and in anaerobic reactors (Riedel and Britz, (1993) Biodiversity and Conservation 2, 400–411). In both cases, the medium proved to be insufficiently selective to enable the propionic bacteria to be counted.

It is apparent from the state of the art as known to the applicant that no medium allows specific counting of propionic bacteria.

The aim of the applicant has thus been to develop a medium allowing specific and relatively rapid counting of propionic bacteria from a biological sample.

In so doing he has found that a culture medium containing lithium as well as polyols and/or antibiotics unexpectedly allows the specific counting of propionic bacteria.

The object of the present invention is thus a medium for the counting under anaerobic conditions of propionic bacteria characterized in that it comprises a complex medium supplemented with, on the one hand, at least one lithium compound and, on the other, at least one polyol and/or one or more antibiotics selected from those to which the propionic bacteria are resistant.

A complex medium should be understood to mean a medium containing at least one multiple nutrient source, such as a yeast extract, a casein hydrolysate or another peptone.

This or these sources contain a high proportion of amino acids and small peptides, as well as vitamins, sugars, purine or pyrimidine bases and other microorganism growth factors.

Preferably, the complex medium used as the base for this counting medium comprises tryptone and yeast extract, for example those supplied by the BIOKAR company.

As a result of the presence of a lithium compound, such a medium inhibits the development of mesophilic and thermophilic lactic bacteria without inhibiting the growth of propionic bacteria. These bacteria can however use and biotransform the polyols contained in the medium into propionic acid.

The lithium compound preferably constitutes between 0.2% and 2% by weight of the medium and the polyol preferably constitutes between 0.01% and 2% by weight of the medium. Such a medium is advantageously used in agar form. It preferably comprises, as lithium compound, lithium lactate, lithium hydroxide or lithium chloride.

If the medium contains lithium lactate, the concentration of this salt may be between 2 and 20 g/l, preferably between 5 and 15 g/l and even more preferably about 10 g/l.

The medium which is the object of the present invention may contain, in addition to the lithium compound, either polyols alone, or one or more antibiotics alone, or a mixture of polyols and antibiotics.

The polyol preferably used in the medium is glycerol or erythritol.

The medium advantageously contains from 0.1 to 20 g/l, preferably from 2 to 10 g/l and even more preferably about 6 g/l, of glycerol.

When the propionic flora are in the minority, for example in milk or cheeses produced from unpasteurized or pasteurized milk, the differentiation of propionic bacteria on a medium according to the invention containing polyols only will prove difficult.

On a medium containing polyols but not antibiotics, the revelation of the presence of propionic bacteria is achieved by the formation of a zone around their colonies where the indicator has changed color, owing to the fermentation of the polyol. In the case of the use of bromocresol purple, for example, the propionic bacteria colonies appear surrounded by a yellow ring on a violet background.

When the extraneous flora are present in significant quantities, the whole of the culture medium changes to pale violet and the differentiation criterion (decoloration of the violet to yellow around the colonies) cannot be used. This is particularly true in the case of counting of "wild" propionic bacteria in unpasteurized milk.

In certain cases, it is thus necessary to increase the selectivity of this medium. This can advantageously be achieved by the addition of antibiotics. In the case where the addition of one or more antibiotics renders the medium totally selective, the addition to the medium of a polyol associated with a colorant to differentiate the propionic bacteria is no longer necessary.

The medium according to the invention advantageously contains one or more antibiotics belonging to the following groups (internationally accepted generic names have been used):

fosfomycin aminosides (gentamycin, kanamycin, tobramycin, etc.)

polypeptides (colistin, polymyxin B, etc.)

first generation quinolones (nalidixic acid, etc.)

second generation quinolones (pefloxacin, norfloxacin, etc.)

imidazoles (metronidazole)

pivmecillinam

The concentrations of each antibiotic are advantageously between 2 and 500 mg/l.

For counting milk propionic bacteria, the antibiotic mixture preferably consists of fosfomycin (2 to 100 mg/l), an antibiotic from the aminoside group (2 to 20 mg/l) and a first generation quinolone (2 to 300 mg/l).

The antibiotics are diluted in an appropriate solvent, sterilized by suitable means and added at the required concentration to the sterilized culture medium.

Unexpectedly, the addition of such an antibiotic cocktail to the YELA medium does not allow the counting of milk propionic bacteria. Although the mechanism has not been established, it seems that the simultaneous presence of such a cocktail and of the lithium salt is necessary to give sufficient selectivity and good growth of the propionic bacteria.

It has also been observed that the growth of propionic bacteria on the medium according to the invention is accelerated by the addition of from 0.05% to 5% of milk to the medium; the addition of 1% of milk to the medium allows the propionic bacteria to be counted after incubation for six days.

It should be noted that, to the knowledge of the applicant the resistance of propionic bacteria to fosfomycin, metronidazole, and pivmecillinam and to second generation quinolones, such as pefloxacin and norfloxacin, has not been described in the prior art.

The present invention also relates to a method for counting bacteria in a biological sample by anaerobic incubation of the said sample or decimal dilutions of it in the medium described above and counting of the said bacteria, by any method known to a person skilled in the art.

For the use of the present invention, reference maybe made, if necessary, to the following manual: GUIRAUD J. GALZY P. (1980). L'analyse microbiologique dans les industries alimentaires. Ed. L'Usine Nouvelle, Paris.

The present invention is illustrated, without in any way being limited, by the following examples:

EXAMPLE 1

Preparation of a counting medium containing glycerol.

To 1000 ml of distilled water were added:

10 g of tryptone (BIOKAR)

10 g of yeast extract (BIOKAR)

10 g of lithium lactate (MERCK)

0.25 g of $K_2HPO_4$ (potassium hydrogen phosphate), 0.05 g of $MnSO_4$ (manganese sulfate) (MERCK) and 0.05 g of bromocresol purple (SIGMA).

Other colored indicators of pH change, such as bromothymol blue, bromocresol green, methyl red or phenol red, may also be used instead of bromocresol purple.

6 g of glycerol were added to the solution obtained, the pH was adjusted to 7.0 by addition of NaOH, and 15 g of type E agar (BIOKAR) were added to the solution. It was brought to boiling with stirring to dissolve the agar, divided into flasks and sterilized by autoclaving for 20 minutes at 115° C.

EXAMPLE 2

Counting of bacteria on the medium from example 1.

a) Comparison of the Counting Medium According to the Invention with YELA Medium.

The capacity of the propionic bacteria belonging to the 4 species found in milk to develop in the culture medium, forming the object of the present invention, was tested in comparison with the YELA reference medium.

The experimental procedure for using the medium according to the invention was the following:

The agar medium obtained according to example 1 was cooled to 46° C. 1 ml of the cultures obtained after 48 hours on YEL medium (YELA without agar), and decimal dilutions of said cultures, were transferred into sterile Petri dishes and covered with 12 ml of the medium. After careful mixing and solidification on a cold surface, the dishes were anaerobically incubated for 5 to 6 days at 30° C.

The propionic bacteria appeared as lenticular or round colonies with diameter equal to or greater than 0.5 mm surrounded by a yellow acidification zone of 1 to 5 mm on a violet background.

The capacity of 42 propionic bacteria strains (table 1), belonging to 4 different species, to develop on the medium forming the object of the present invention was tested in comparison with the YELA reference medium.

It was observed that the culture medium forming the object of the present invention led to count values for propionic bacteria cultures that were very close to if not identical with those obtained with the YELA reference medium.

b) Counting of Bacteria from Different Species

The selectivity of the medium forming the object of the present invention was tested in comparison with 18 bacterial species (table 2), representative of lactic and milk-contaminating flora or of their derivatives, and compared with 6 commercial mixtures of mesophilic and thermophilic lactic ferments.

1 ml of 48-hour cultures of the different species to be tested and of decimal dilutions of said cultures were transferred into sterile Petri dishes. The experimental procedure was then the same as that described above.

c) Counting in Milk.

The selectivity of the culture medium forming the object of the present invention was tested in comparison with the YELA reference medium on ultra-pure milk (unpasteurized skim milk micro-filtered on a membrane with pore diameter 1.4 microns) to which had been added 500 ml of a culture of propionic bacteria with concentration $2.6 \times 10^9$ cells/ml to 15 000 1 of milk (corresponding to an inoculation level of approximately $1 \times 10^5$ propionic bacteria cells per ml of milk). The said milk was also inoculated with $1 \times 10^6$ mesophilic and thermophilic lactic bacteria per ml. The counts carried out with the two media led to the following results:

YELA medium: $1.7 \times 10^6$ CFU/ml medium according to the invention: $4.5 \times 10^5$ CFU/ml The medium according to the invention led to a propionic bacteria count very close to that resulting from the addition of the pure culture to the milk while the YELA medium gave a value nearly 4 times higher.

d) Counting in Pressed-Crust Cheeses.

The selectivity of the culture medium forming the object of the present invention was also tested on different pressed-crust cheeses. To do this, 10 g of cheese were added to 90 ml of citrate solution (solution of 20 g of trisodium citrate in 1000 ml of distilled water adjusted to pH 7.5 by the addition of sodium hydroxide). The suspension was ground for 3 minutes in a Stomacher and then used to inoculate the media according to the invention and YELA as described above. The results are given in table 3 below.

EXAMPLE 3

Resistance of Propionic Bacteria to Antibiotics

The five typical strains of milk propionic bacteria were tested for their resistance to 27 antibiotics. These tests were carried out by means of ATB galleries (BioMérieux, Marcy-L'Etoile, France) after 48 hours culture on YEL broth and appropriate dilution according to the manufacturer's recommendations. The incubation of the galleries was carried out anaerobically at 30° C. for 30 hours. The growth of the propionic bacteria was evaluated semi-quantitatively by observation of the degree of cloudiness in each cup (table 4).

This table shows in particular very good resistance of the strains used to the aminosides tested, to fosfomycin, to first and second-generation quinolones and to colistin, metronidazole and oxacillin.

EXAMPLE 4

Preparation of the Counting Medium Containing Antibiotics.

Three antibiotic solutions were prepared by the addition in distilled water of the following quantities:

solution F: fosfomycin (Sigma P5396) 256.0 mg qsp 50 ml distilled water.

solution G: gentamycin (Sigma P3632) 32.0 mg qsp 100 ml distilled water. solution N: nalidixic acid (Sigma N 8878) 64.0 mg qsp 20 ml distilled water in basic medium (addition of NaOH).

Solutions F, G, N and distilled water were mixed in the proportions 5:10:2:23. The mixture was then filtered under sterile conditions, divided into sterile tubes and stored at -20° C.

A stock tube of the antibiotic mixture was thawed when required for use. Five milliliters of this mixture were added to 95 ml of the sterile agar medium according to example 1, the latter having been cooled to 46° C. The dilution factor resulting from the addition of the antibiotic solution was taken into account when preparing the agar medium (prepared in 950 ml with sufficient quantities for one liter).

EXAMPLE 5

Counting of propionic bacteria in pure culture on the medium according to example 4.

Twenty-four Propionibacterium strains belonging to the five milk species were tested for their capacity to develop on the culture medium according to example 4, in comparison with their growth on YELA medium. The counting was carried out after 48 hours culture on YEL broth. One milliliter of the appropriate decimal dilutions of these cultures was transferred into sterile Petri dishes. The experimental procedure was then the same as that described in example 2. The results are given in table 5.

The difference between the count values on YELA and on the medium according to the invention was on average 0.2 in decimal logarithms.

After 6 days incubation, two-thirds of the strains tested showed colonies with typical appearance (colony diameter greater than or equal to 0.5 mm and presence of a decolorized zone of 1 to 5 mm around the colonies), or conformed to one of these two criteria. When the length of incubation was increased to 8 days, both criteria (colony diameter and decolorized zone) were observed for almost all the strains tested.

EXAMPLE 6

Effect of the Addition of Milk to the Culture Media According to Examples 1 and 4.

The addition of milk to the culture medium containing antibiotics according to the invention increased the speed of growth and enabled the incubation time necessary for observing the typical characteristics of propionic bacteria colonies to be reduced.

Table 6 gives the results obtained with the strain Propionibacterium freudenreichii subsp. shermanii CIP 103027.

Counting was carried out after 48 hours as described in example 5.

The addition of 0.1% to 1% of autoclaved skim milk to the culture medium according to example 4 was carried out before transfer into the Petri dishes. The results are given in table The addition of 1% of milk resulted in the production of colonies with size equal to or greater than those obtained on YELA medium and in addition encouraged the production of colonies showing a marked decoloration zone after 6 days incubation.

EXAMPLE 7

Comparative Counting of Milk Propionic Bacteria on YELA Medium and on the Media of Examples 1 and 4.

The selectivity of the medium containing antibiotics forming the object of the present invention was tested in comparison with the same medium without antibiotics and the YELA reference medium.

For 21 samples of homogenized milk, 1 ml of milk and decimal dilutions of said samples were transferred into sterile Petri dishes. The experimental procedure was then the same as that described in example 2.

Table 7 gives the results for the counts of propionic bacteria in homogenized milk by means of YELA medium, the medium according to example 1 (lithium-glycerol medium) and the medium according to example 4 (lithium-glycerol-antibiotics medium). For each medium, two separate counts were carried out after 6 days anaerobic incubation:

1. the count of all microorganisms able to develop on this medium;
2. the count of propionic bacteria colonies, defined according to the following criteria:

on YELA and lithium-glycerol medium, cream-colored lenticular or round colonies with diameter greater than or equal to 0.5 mm, on lithium-glycerol-antibiotics medium, lenticular or round colonies with diameter greater than or equal to 0.5 mm surrounded by a yellow acidification zone of 1 to 5 mm on a violet background.

The increase in selectivity introduced by the addition of the antibiotics to the lithium medium is shown by this table.

The difference between the propionic flora and the total flora able to develop on the lithium-glycerol-antibiotics medium was on average 0.10 in decimal logarithms.

EXAMPLE 8

Combined Effect of Lithium and Antibiotics.

A comparative count was carried out for samples of homogenized milk:

on YELA medium with or without lithium and/or antibiotics in the same proportions as those given in example 4, on the medium according to example 1 (lithium-glycerol medium), on the medium according to example 4 (lithium-glycerol-antibiotics medium).

The experimental procedure was identical to that used in example 7. The results are given in table 8.

This clearly shows that the simultaneous addition of lithium and the antibiotic cocktail used gives the maximum selectivity, while no typical colony could be observed on the YELA medium with the antibiotic cocktail alone.

Through its selectivity and electivity, the culture medium forming the object of the present invention can be used to:

1) carry out the rapid isolation of new strains of propionic bacteria which can then be characterized by their technological properties (production of $CO_2$, propionic acid, vitamin $B_{12}$);

2) determine the endogenous propionic flora of collected milk so that its level can, if necessary, be adjusted;

3) monitor the development of the propionic flora in pressed-crust cheeses.

In conclusion, the use of this medium enables the improvement of the overall quality of the manufacture of pressed-crust cheeses or of other new varieties of cheese.

TABLE 1

Counting of propionic bacteria log cfu/ml

| Species | Strain | YELA medium | Medium according to the invention | Acidification zone $\phi$ in mm |
|---|---|---|---|---|
| P. freudenreichii | CIP 5932 | 8.23 | 8.26 | NA* |
| | CIP 103026 | 7.88 | 7.80 | 2 |
| | CIP 103027 | 8.59 | 8.65 | 5 |
| | CNRZ 81 | 9.41 | 9.43 | 6 |
| | CNRZ 89 | 8.95 | 8.90 | 6 |
| | CNRZ 728 | 7.84 | 8.00 | 2 |
| | CNRZ 434 | 8.92 | 9.00 | 3 |
| | CNRZ 277 | 9.05 | 8.95 | 0.5 |
| | NCDO 839 | 9.44 | 9.45 | 5 |
| | NCDO 853 | 9.65 | 9.27 | 5 |
| | NCDO 1081 | 9.46 | 9.42 | 2 |
| | NCIB 9885 | 9.74 | 9.65 | 5 |
| | DSM 20270 | 9.69 | 9.65 | 5 |
| | NCIB 9416 | 9.61 | 9.36 | 1 |
| | ATCC 9617 | 9.46 | 9.48 | 5 |
| P. jensenii | CIP 103028 | 8.00 | 8.08 | 5 |
| | CIP 6435 | 8.54 | 8.49 | 3 |
| | CNRZ 83 | 9.90 | 9.88 | 1 |
| | CNRZ 79 | 9.62 | 9.66 | 2 |
| | CNRZ 87 | 9.40 | 9.29 | 2 |
| | CNRZ 730 | 9.98 | 10.02 | 1.5 |
| | CNRZ 288 | 8.52 | 8.47 | 1 |
| | CNRZ 851 | 9.89 | 8.82 | 2 |
| | NCDO 1077 | 8.78 | 8.68 | 2 |
| | NCDO 1074 | 9.49 | 9.31 | 0.5 |
| | NCDO 1078 | 8.97 | 8.91 | 2.5 |
| P. thoenii | CIP 103029 | 6.30 | 6.30 | 3 |
| | CIP 6434 | 6.60 | 6.90 | 2 |
| | CNRZ 85 | 7.92 | 7.86 | 2 |
| | CNRZ 732 | 9.93 | 9.92 | 2 |
| | CNRZ 84 | 9.94 | 9.88 | 1 |
| | NCDO 1080 | 9.06 | 9.40 | 3 |
| | NCDO 1082 | 7.81 | 7.84 | little AC++ |
| P. acidi propionici | NCDO 852 | 8.32 | 8.24 | 2 |
| | NCDO 1072 | 8.54 | 8.65 | NA |
| | DSM 4900 | 8.17 | 8.22 | 3 |
| | DSM 20273 | 9.00 | 9.06 | 6 |
| | CNRZ 86 | 8.54 | 8.70 | 5 |
| | CNRZ 80 | 8.08 | 8.16 | 1.5 |
| | ENT P01 | 9.13 | 9.04 | 2 |
| | ENT 4875 | 9.19 | 9.22 | NA |
| | ATCC 25562 | 7.81 | 7.65 | 2 |
| Industrial strains | LABO STANDA lyophilized 0.1 g - 10 ml peptone-water | | | |
| | 2408 | 9.95 | 9.89 | 1 |
| | 2410 | 8.23 | 8.09 | 3 |
| | 2500 | 9.89 | 9.91 | 2 |
| | 2501 | 10.02 | 9.99 | 2 |
| | 2502 | 10.01 | 10.03 | 1.5 |
| | 2503 | 8.43 | 8.5 | 2.5 |

*non-acidifying
++little acidification

TABLE 2

Evaluation of the selectivity of the medium

| Microorganism tested | No species | No of strains/ species | Growth | No of decimal reductions compared to YELA medium | Colony size | Acidification | Conclusions |
|---|---|---|---|---|---|---|---|
| Lactococcus | 3 | 2 | − | | — | — | |
| Lacobacillus | 7 | 1 to 2 | exc Lb plantarum Lb fermentum 0 | 0 | 1.5 0.3 mm | + | Selective medium |
| S. thermophilus | 1 | 2 | − | | — | | |
| Leuconostoc | 1 | 1 | − | | | | |
| lactis | | 2 | + | 0 to 5 | 0.2–0.3 mm | — | |
| Brevibacterium linens | 1 | 2 | − | | — | | |
| Micrococcus | 2 | 1 | + | 0 | 0.2–0.5 mm | | Selective medium |
| Citrobacter | 1 | 1 | + | 0 | 3–4 mm | — | |
| E. coli | 1 | 1 | + | 0 | 1 mm | — | |
| Clost. spirogenes | 1 | 1 | + | 0 | 1 mm | — | |
| Commercial ferments | | | | | | | |
| EZAL MYO 87 | | 2 tests | − | | — | — | Selective medium |
| EZAL MM 101 | | 2 tests | + | 3–4.5 | 0.2 mm | — | |
| EZAL MA 019 | | 2 tests | + | 2–4 | 0.2 mm | | |
| Flora Danica | | 1 test | + | 5 | 0.2 mm | — | No acidification zones |
| EZAL TA 040 | | 1 test | + | 2.5 | 0.2 mm | — | colony sizes <0.5 mm |
| EZAL TA 060 | | 1 test | + | 1 | 0.2 mm | — | |

TABLE 3

| Cheeses | Medium | Counts CFU/g Medium according to the invention | YELA |
|---|---|---|---|
| Emmental 13 days old, cool cellar | | $4.9 \times 10^6$ | $7.6 \times 10^6$ |
| Emmental, commercial grand cru | | $7.0 \times 10^8$ | $1.3 \times 10^9$ |
| Beaufort, matured 18 months | | $3.0 \times 10^4$ | $1.1 \times 10^8$ |
| Swiss Fribourg, commercial | | $1.3 \times 10^4$ | $1.4 \times 10^6$ |
| Morbier | | $1.1 \times 10^9$ | $2.5 \times 10^9$ |

TABLE 4

Resistance of propionic bacteria to antibiotics (1)

| Family | Antibiotic (mg/l) | Strains CIP 103026 | CIP 103027 | CIP 103028 | CIP 103029 | DSM 4900 |
|---|---|---|---|---|---|---|
| BETALACTAMINES | | | | | | |
| PENICILLIN Group G | Penicillin (0.25/16) | 4/0 | 3/0 | 3/0 | 0/0 | 4/0 |
| PENICILLIN Group M | Oxacillin (2) | 4 | 4 | 4 | 3 | 4 |
| AMINO-PENICILLIN | Amoxicillin (4/16) | 0/0 | 0/0 | 0/0 | 0/0 | 0/0 |
| PIVMECILLINAM | Pivmecillinam (2/8) | 4/4 | 4/4 | 4/4 | 4/4 | 3/3 |
| CEPHALOSPORIN 1° G | Cephalothin (8/32) | 1/0 | 0/0 | 0/0 | 0/0 | 0/0 |
| CEPHALOSPORIN 2° G | Cefoxitin (8/32) | 4/4 | 4/2 | 4/2 | 0/0 | 2/0 |
| CEPHALOSPORIN 3° G | Cefotaxime (4/32) | 2/0 | 0/0 | 0/0 | 0/0 | 0/0 |
| AMINOSIDES | Kanamycin (8/16) | 4/4 | 4/4 | 4/4 | 4/4 | 4/4 |
| | Tobramycin (4/8) | 4/4 | 4/4 | 4/4 | 4/4 | 4/4 |
| | Gentamycin (4/8) | 4/4 | 4/4 | 4/4 | 4/2 | 4/4 |
| | Netilmicin (4/8) | 4/4 | 4/4 | 4/4 | 4/3 | 4/4 |
| PHENICOLS | Chloramphenicol (8/16) | 0/0 | 0/0 | 0/0 | 0/0 | 0/0 |
| CYCLINES | Tetracycline (4/8) | 0/0 | 0/0 | 0/0 | 0/0 | 0/0 |
| MACROLIDES and derivatives | Erythromycin (1/4) | 0/0 | 0/0 | 0/0 | 0/0 | 4/3 |
| | Lincomycin (2/8) | 3/0 | 4/0 | 0/0 | 0/0 | 2/0 |
| | Clindamycin (2) | 0 | 0 | 0 | 0 | 0 |
| | Pristinamycin (2/4) | 0/0 | 0/0 | 0/0 | 0/0 | 0/0 |

TABLE 4-continued

Resistance of propionic bacteria to antibiotics (1)

| | | Strains | | | | |
|---|---|---|---|---|---|---|
| Family | Antibiotic (mg/l) | CIP 103026 | CIP 103027 | CIP 103028 | CIP 103029 | DSM 4900 |
| RIFAMYCINS | Rifampicin (4/16) | 0/0 | 0/0 | 0/0 | 0/0 | 0/0 |
| POLYPEPTIDES | Colistin (4) | 4 | 4 | 4 | 4 | 4 |
| IMIDAZOLES | Metronidazole (4) | 4 | 4 | 4 | 4 | 4 |
| SULFAMIDES | Co-trimoxazole (2/8) | 2/1 | 2/1 | 0/0 | 0/0 | 0/0 |
| QUINOLONES 1° G | Nalidixic acid (8/16) | 4/4 | 4/4 | 4/4 | 4/4 | 4/4 |
| QUINOLONES 2° G | Pefloxacin (1/4) | 4/3 | 3/0 | 4/3 | 4/1 | 4/1 |
| | Norfloxacin (1/8) | 4/4 | 4/4 | 4/4 | 4/1 | 4/4 |
| GLYCOPEPTIDES | Vancomycin (4/8) | 0/0 | 0/0 | 0/0 | 0/0 | 0/0 |
| OTHERS | Fosfomycin (32/64) | 4/4 | 4/4 | 4/3 | 4/3 | 4/4 |
| | Fusidic acid (2/16) | 0/0 | 0/0 | 0/0 | 0/0 | 0/0 |

(1) The growth was graded from 0 (no growth) to 4 (growth equivalent to that observed on a control medium without antibiotic).

TABLE 5

Counting of propionic bacteria

| | | Log CFU/ml (after 6 d incubation) | | |
|---|---|---|---|---|
| Species | Strains | YELA | Medium according to the invention* | Difference (log) |
| *P. freud* | CIP 5932 | 9.79 | 9.71 | −0.08 |
| subsp | CNRZ 81 | 9.43 | 8.99 | −0.44 |
| *freudenreichii* | CNRZ 89 | 8.78 | 8.48 | −0.30 |
| | CNRZ 435 | 9.40 | 9.30 | −0.10 |
| *P. freud.* | CNRZ 725 | 9.83 | 9.70 | −0.13 |
| subsp. | NCDO 277 | 10.00 | 9.92 | −0.08 |
| *shermanii* | NCDO 434 | 9.94 | 9.92 | −0.02 |
| | NCDO 853 | 10.06 | 9.33 | −0.73 |
| | NCDO 839 | 9.85 | 9.83 | −0.02 |
| | NCDO 1081 | 9.88 | 10.00 | 0.12 |
| | CIP 103027 | 9.64 | 9.18 | −0.46 |
| | ENT 13673 | 9.83 | 9.82 | −0.01 |
| *P. jensenii* | CIP 103028 | 10.11 | 10.07 | −0.04 |
| | NCDO 851 | 9.79 | 8.84 | −0.95 |
| | NCDO 1074 | 9.91 | 9.90 | −0.01 |
| *P. thoenii* | CIP 103029 | 10.11 | 9.76 | −0.35 |
| | CIP 6434 | 9.66 | 9.68 | 0.02 |
| | CNRZ 732 | 10.14 | 9.85 | −0.29 |
| | NCDO 1080 | 9.35 | 9.39 | 0.04 |
| *P. acidipropionici* | DSM 4900 | 9.67 | 9.40 | −0.27 |
| | DSM 20273 | 9.64 | 9.58 | −0.06 |
| | CNRZ 80 | 9.79 | 9.60 | −0.19 |
| | CNRZ 86 | 9.41 | 9.48 | 0.07 |
| | ENT 4875 | 9.38 | 9.56 | 0.18 |

*according to example 4

TABLE 6

Effect of the addition of milk on colony counts and sizes
(strain *P. freudenreichii* CIP 103027)

| | Log (CFU/ml) (Colony diameters) | | |
|---|---|---|---|
| Culture medium | 0% milk | 0.1% milk | 1% milk |
| YELA | 9.64 | 9.72 | 9.71 |
| | (0.8 to 2 mm) | (0.8 to 2 mm) | (0.8 to 2 mm) |
| Medium according to example 1 | 9.61* | 9.58* | 9.48* |
| | (1.0 to 1.5 mm) | (1.0 to 2 mm) | (1.0 to 2 mm) |
| | decoloration zone | decoloration zone | decoloration zone |
| Medium according to example 4 | 9.18** | 9.25*** | 9.43* |
| 6 days | (0.2 to 1 mm) | (1.0 to 2.0 mm) | (1.0 to 1.5 mm) |
| incubation | no or little decoloration zone | little decoloration | decoloration zone |
| Medium according to | 9.65*** | 9.62*** | 9.57* |

TABLE 6-continued

Effect of the addition of milk on colony counts and sizes
(strain *P. freudenreichii* CIP 103027)

| | Log (CFU/ml) (Colony diameters) | | |
|---|---|---|---|
| Culture medium | 0% milk | 0.1% milk | 1% milk |
| example 4 | (0.2 to 3 mm) | (0.2 to 3 mm) | (1.5 to 3 mm) |
| 8 days | decoloration zone | decoloration zone | decoloration |
| incubation | | | |

*typical colonies
**atypical colonies
***+/− typical colonies

TABLE 7

Counting of milk propionic bacteria log (colony forming units/ml)

| | Total countable flora | | | Propionic flora | | |
|---|---|---|---|---|---|---|
| Samples | YELA | example 1* | example 4* | YELA | example 1* | example 4* |
| 1 | 6.90 | 5.90 | 3.11 | 2.78 | 2.75 | 2.90 |
| 2 | 6.19 | 5.18 | 2.62 | 2.86 | 2.73 | 2.62 |
| 3 | 5.61 | 5.23 | 3.00 | 3.00 | 3.05 | 3.00 |
| 4 | 5.45 | 5.00 | 2.70 | 2.64 | 2.59 | 2.70 |
| 5 | 4.85 | 4.60 | 2.92 | 2.92 | 2.91 | 2.92 |
| 6 | 5.52 | 5.40 | 2.96 | 3.07 | 3.06 | 2.73 |
| 7 | 4.61 | 4.51 | 3.45 | nd | 3.59 | 3.45 |
| 8 | 3.90 | 3.86 | 2.63 | 2.56 | 2.04? | 2.53 |
| 9 | 3.70 | 3.70 | 2.50 | 2.15 | 2.30 | 2.30 |
| 10 | 3.80 | 3.80 | 2.80 | 3.20 | 3.30 | 2.80 |
| 11 | 3.90 | 3.70 | 2.50 | nd | 2.60? | 2.30 |
| 12 | 3.45 | 3.46 | 2.36 | 2.30 | 2.23 | 1.90 |
| 13 | 3.60 | 3.54 | 2.59 | 2.20 | 2.26 | 2.51 |
| 14 | 4.05 | 3.50 | 1.90 | 1.30 | 2.30? | 1.90 |
| 15 | 3.60 | 3.40 | 2.60 | 2.51 | 2.46 | 2.60 |
| 16 | 4.04 | 3.85 | 2.83 | 2.00 | 2.61 | 2.73 |
| 17 | 3.10 | 3.00 | 2.40 | 2.26 | 2.59 | 2.20 |
| 18 | 3.70 | 3.80 | 2.08 | nd | 3.30? | 1.90 |
| 19 | 3.30 | 2.30 | 1.10 | nd | 1.30 | 1.00 |
| 20 | 3.10 | 2.60 | 1.80 | 2.00 | 1.85 | 1.73 |
| 21 | 2.80 | 1.50 | 0.70 | 0.5? | 1.26? | 0.60 | nd: not determinable
x?: non-typical colonies, value not certain
*medium according to the invention

TABLE 8

Counting of milk propionic bacteria
(combined effect of lithium and antibiotics)

| | Log (CFU/ml) | |
|---|---|---|
| | Total countable flora | Propionic flora |
| Medium | | |
| YELA | 4.01 | 2.90? |
| YELA + antibiotics* | 3.45 | nd |
| YELA + lithium | 3.85 | 2.69? |
| Media according to the invention | | |
| YELA + lithium + antibiotics | 3.20 | 2.78 |
| medium according to example 1 | 3.72 | 2.70? |
| medium according to example 4 | 3.00 | 2.62 | nd: not countable (no typical colony)
x?: colonies with diameter greater than 0.5 mm (counting uncertain)
*antibiotics mixture according to example 4

We claim:

1. A composition useful for counting propionic bacteria under anaerobic conditions and which composition comprises a complex medium for culturing said propionic bacteria supplemented with a) at least one lithium compound and b) at least one polyol or antibiotic selected from antibiotics to which the propionic bacteria are resistant.

2. A composition according to claim 1, wherein the complex medium comprises a mixture of a casein hydrolysate and a yeast extract.

3. A composition according to claim 1, which is in agar form.

4. A composition according to claim 1, which contains from 0.2% to 2% by weight of the medium of a lithium compound and from 0.01% to 2% by weight of the medium of a polyol.

5. A composition according to claim 1, wherein the lithium compound is lithium lactate, lithium hydroxide or lithium chloride.

6. A composition according to claim 5, which contains between 2 and 20 g/l of lithium lactate.

7. A composition according to claim 1, wherein the polyol is glycerol or erythritol.

8. A composition according to claim 7, which contains between 0.1 to 20 g/l of glycerol.

9. A composition according to claim 1, which comprises about:

10 g of tryptone 10 g of yeast extract 10 g of lithium lactate 0.25 of $K_2HPO_4$ 0.05 g of $MnSO_4$ 15 g of agar 0.05 g of bromocresol purple 1000 ml of water, and the medium has a pH adjusted to 7.

10. A composition according to claim 1, which contains one antibiotic.

11. A composition according to claim 1, wherein the concentration of the at least one antibiotic is between 2 and 500 mg/l.

12. A composition according to claim 1, which contains between 0.05% and 5% of milk.

13. In a method for counting propionic bacteria in a biological sample, the improvement which comprises anaerobically incubating said sample or a decimal dilution thereof in a medium according to claim 1 before counting said bacteria.

14. A composition according to claim 6 containing between 5 and 15 g/l of lithium lactate.

15. A composition according to claim 6 containing about 10 g/l of lithium lactate.

16. A composition according to claim 8 containing from 2 to 10 g/l of glycerol.

17. A composition according to claim 8 containing about 6 g/l of glycerol.

18. A composition according to claim 10 wherein the antibiotic is a member selected from the group consisting of fosfomycin, an aminoside, a polypeptide, a first-generation quinolone, a second-generation quinolone and an imidazole.

* * * * *